United States Patent [19]

Stühler et al.

[11] Patent Number: 4,521,595

[45] Date of Patent: Jun. 4, 1985

[54] PROCESS FOR THE PURIFICATION OF ESTERS

[75] Inventors: Herbert Stühler; Engelbert Krempl, both of Burgkirchen, Fed. Rep. of Germany

[73] Assignee: Hoechst Aktiengesellschaft, Fed. Rep. of Germany

[21] Appl. No.: 399,195

[22] Filed: Jul. 16, 1982

[30] Foreign Application Priority Data

Jul. 21, 1981 [DE] Fed. Rep. of Germany ....... 3128696

[51] Int. Cl.$^3$ .............................................. C07H 1/06
[52] U.S. Cl. ................................. 536/127; 260/410.6; 260/412; 536/115; 536/116; 536/119; 536/124; 560/248
[58] Field of Search ............... 536/115, 114, 119, 116, 536/124, 127, 63, 66, 68, 84, 91; 260/410.6, 412; 560/248

[56] References Cited

U.S. PATENT DOCUMENTS

| | | | |
|---|---|---|---|
| 3,275,576 | 9/1966 | Flodin et al. | 536/120 |
| 3,600,378 | 8/1971 | Marsh et al. | 536/127 |
| 4,076,930 | 2/1978 | Ellingboe et al. | 536/120 |
| 4,090,919 | 5/1978 | Chibata et al. | 536/120 |
| 4,306,062 | 12/1981 | Jones | 260/410.6 |
| 4,350,572 | 9/1982 | Kummer et al. | 560/248 |
| 4,377,686 | 3/1983 | Feuge et al. | 536/119 |

Primary Examiner—Johnnie R. Brown
Attorney, Agent, or Firm—Connolly & Hutz

[57] ABSTRACT

A process for the purification of esters, which contain residues of dissolved and/or undissolved alcohols, is described. The purification of the esters containing alcohols is achieved by treating the esters, in the liquid state, with an effective amount of water-soluble polysaccharide derivatives in the solid state.

8 Claims, No Drawings

PROCESS FOR THE PURIFICATION OF ESTERS

The invention relates to a process for the purification of esters which contain alcohols, by which the alcohols contained in the ester can be removed in a simple manner.

Esters, in the preparation of which alcohols are used or are formed, generally still contain residual amounts of alcohol, even after the customary working-up processes for separating out the ester from the reaction product. Esters are obtained which still contain small amounts of alcohol even in those processes for preparation in which the alcohol is not used in excess but in the stoichiometric ratio, and even in those reactions with which it is only intended to modify an ester, for example, in an oxalkylation. The presence of alcohol frequently leads to a cloudiness of the ester which is per se clear. In this case, the alcohol is present substantially in the form of dispersed particles (droplets of liquid) in the ester. This cloudiness of esters due to the presence of alcohols is understandably very undesirable for several reasons. It can, for example, significantly adversely affect the chemical and physical properties of the ester. In addition, it adversely affects the visual appearance. All this leads to a noticeable decrease in quality.

The alcohol residues in esters can also be present in the dissolved form. Even though in this case no cloudiness occurs, and the ester is clear, the presence of alcohol is frequently undesirable for the reason that the chemical and physical properties of the esters are changed.

The known processes for the purification of esters (crude esters) from alcohol constituents are industrially costly, especially because the amounts of alcohol present in the crude ester, which are to be removed, are relatively small. In addition, with the known processes, the purification achieved is frequently unsatisfactory, and in particular, not even the complete removal of the cloudiness of the ester is achieved.

According to the process known from German Pat. No. 1,181,692, attempts are made to remove the alcohol from the crude ester by steam distillation carried out under specific conditions, and according to the process known from German Offenlegungsschrift No. 2,423,278, removal is attempted by extraction with water. These methods are not only industrially costly, but satisfactory purification is not always achieved with them. Furthermore, steam distillation fails as a purification operation in all those cases in which the alcohol to be distilled off is not steam-volatile, as is the case, for example, when the alcohol components are polyglycerols.

The treatment of esters with active charcoal, aluminum oxide, fuller's earth and silica gels in order to improve the chemical and physical properties, for example to decrease the water content and the acidity, to dry completely, to increase the electrical resistance (in particular of esters which are used as plasticizers in plastics for cable coverings) and to increase the color quality is also known, for example from German Pat. No. 1,007,314, the abovementioned German Offenlegungsschrift No. 2,423,278 and U.S. Pat. No. 3,637,774. In respect of the alcohols present in the ester, these agents bring about unsatisfactory purifying effects, if any at all.

Thus the object of the invention is to provide a process by which purification of esters from alcohol constituents is achieved and which is simple to carry out. It should, in particular, convert esters, which appear cloudy due to the presence of alcohol, into clear products. In addition, it should be possible also to remove substantially or completely alcohol constituents dissolved in the ester.

This object is achieved according to the invention by treating the ester (containing alcohol) in the liquid form with an effective amount of water-soluble polysaccharide derivatives in the solid form.

Surprisingly, by the treatment according to the invention, not only is the alcohol, which is dispersed in the ester and thus produces an undesired cloudiness, removed in a rapid and simple manner, whereby esters of high clarity are obtained, but alcohols present in the dissolved form can also be removed, either substantially or completely, as desired. This result could not have been expected since even dispersed alcohol, and certainly dissolved alcohol, cannot be readily removed with a wide variety of known absorbents, such as aluminum oxides, active charcoals, silica gels and fuller's earths.

In the treatment according to the invention, water-soluble polysaccharide derivatives are used in the solid form. Of these polysaccharide derivatives, preferably the alkyl, hydroxyalkyl and carboxyalkyl ethers of cellulose, of starch and of guar (guar gum) and their mixed ethers are employed, in this context alkyl being a group having preferably 1 to 3 C atoms, hydroxyalkyl being a group having preferably 2 to 4 C atoms and carboxyalkyl being a group having preferably 2 to 3 C atoms (the alkyl group in "hydroxyalkyl" is thus preferably the ethylene, propylene or butylene group and the alkyl group in "carboxyalkyl" is preferably —$CH_2$— or —$CH_2CH_2$—). The particularly preferred carboxyalkyl ethers and carboxyalkyl mixed ethers of cellulose, of guar and of starch can be employed as such, or in the form of salts, preferably of alkali metal salts, in particular as sodium salts, and they are preferably employed in the salt form.

Individual polysaccharide ethers which may be mentioned as suitable, and advantageously used, are: methylcellulose, ethylcellulose, propylcellulose, hydroxyethylcellulose, hydroxypropylcellulose, hydroxybutylcellulose, hydroxyethylmethylcellulose, hydroxyethylethylcellulose, hydroxypropylmethylcellulose, hydroxybutylmethylcellulose, carboxymethylcellulose, carboxymethylmethylcellulose, hydroxyethylcarboxymethylcellulose and hydroxypropylcarboxymethylcellulose and their sodium salts and the analogous ethers of guar and starch.

The polysaccharide derivatives to be used according to the invention are known and obtainable commercially. They are available as a rule in the solid form, as a powder or as granules, and are water-soluble, preferably at room temperature. Their viscosity, measured in a 2% strength aqueous solution, varies within wide limits (cf. Ullmanns Enzyklopädie der technischen Chemie (Encyclopedia of Industrial Chemistry) volume 9, 4th edition, Verlag Chemie, Weinheim, Federal Republic of Germany).

Water-soluble polysaccharide derivatives are employed in the treatment according to the invention, in solid form, preferably as a powder and/or as ganules. The water-soluble polysaccharide derivatives can, where advantageous, be employed as a paste which is obtained by mixing with a little water. The viscosity, the degree of substitution and the type of substitution of the polysaccharide derivatives is not critical, as long as they are water-soluble.

The amount of polysaccharide derivative to be used in the process according to the invention can vary within wide limits. An amount will be employed which is effective for the degree of purity desired in each case. If the object is only to remove that alcohol constituent which gives rise to the cloudiness of the ester, a relatively small amount of polysaccharide derivative is generally necessary. In contrast, if not only the alcohol constituent causing the cloudiness but also the dissolved alcohol constituent is to be removed, then larger amounts are necessary. This also applies when the alcohol is only present in the dissolved form and is to be removed. The effective amount of polysaccharide derivative is thus, in general, 0.01 to 20% by weight, preferably 0.1 to 10% by weight, relative to the weight of the ester to be purified. As a rule, 0.01 to 5% by weight, preferably 0.1 to 3% by weight, relative to the weight of the ester to be purified, suffices to remove the alcohol responsible for cloudiness. For the removal of alcohol responsible for cloudiness and dissolved alcohol, or only of dissolved alcohol (where cloudiness is not present), the amount of polysaccharide derivative is generally 5 to 20% by weight, preferably 10 to 15% by weight, relative to the weight of ester to be purified.

In the process according to the invention, the ester to be purified are treated with an effective amount of water-soluble solid polysaccharide derivatives. For this purpose, the esters must be in the liquid form. When they are not themselves already liquid, the liquid state can be simply achieved by heating to above the melting point of the ester which is in the solid or almost solid (viscous to highly viscous) form. The treatment according to the invention can be carried out in accordance with various procedures. It is only determined by bringing the ester to be purified, in the liquid form, into contact with the water-soluble polysaccharide derivative to be used in the solid form (once or several times, continuously or discontinuously), until the desired degree of purity is reached, when the polysaccharide derivative is separated off, preferably by filtration or by decantation, and the (clear) ester is obtained, which has been purified entirely from the alcohol responsible for cloudiness and, to the desired extent, from the dissolved alcohol. The process of bringing into contact is promoted in an advantageous manner by stirring. For this reason, the ester should be in a liquid form, i.e. it should flow readily and be relatively easily stirred.

The time during which the ester to be purified is in contact with the polysaccharide derivative employed can vary within these limits. Obviously, it depends on the amount of polysaccharide derivative employed and on whether or not stirring is carried out, and can range from a few minutes up to several hours. As a rule, it is 5 to 120 minutes, preferably 10 to 60 minutes.

The temperature during treatment can vary within wide limits. It is substantially determined by the constitution of the ester to be purified. If this is itself liquid, the treatment is generally carried out at room temperature (15° to 25° C.). If it is solid or very viscous, the treatment is carried out at that temperature at which the ester is in the liquid (low viscosity, filterable) form, i.e. at an appropriately advantageous temperature above the melting point of the ester. The temperature of the ester during treatment is thus advantageously 15° to 90° C. Advantageously, the treatment is generally carried out without the application of pressure, but it can also be undertaken under pressure.

The treatment according to the invention is preferably carried out in such a manner that the polysaccharide derivative, in the form of a powder or granules, is added all at once or in portions to the liquid ester in a vessel, with stirring. After the addition, stirring is continued as a rule for 5 to 120 minutes, preferably 10 to 60 minutes. Subsequently, the polysaccharide derivative is filtered off or it is allowed to settle out and decantation is carried out (if the ester is solid at room temperature, it can be cooled down again after filtration or decantation). The ester treated by the process according to the invention is a clear liquid or a solid product, which has been totally or partially purified of alcohol constituents, and is also a clear liquid in the molten state.

The process according to the invention can be used for any ester. It is, as already mentioned above, only necessary that it be in the liquid form during the treatment according to the invention. The process is preferably used for those esters in which the alcohol component is an alcohol which has at least one hydroxyl group forming hydrogen bonds and in which the acid component is substantially insoluble; the acid in the acid component is not critical. The acid component can be a natural or a synthetic acid. As a rule, it is an aliphatic carboxylic acid, preferably an aliphatic monocarboxylic acid, which can be straight-chain or branched and saturated or unsaturated (preferably singly to triply unsaturated). Particularly preferred acid components are fatty acids having 4 to 22 C atoms, preferably having 8 to 18 C atoms, such as lauric acid, myristic acid, palmitic acid, stearic acid, oleic acid, linoleic acid and the corresponding isoacids. As a rule, the alcohol component is an aliphatic alcohol having one or more, preferably 1 to 20 hydroxyl groups (monohydric and polyhydric alcohols), the chemical structure of the monohydroxylalcohols and the polyols (diols, triols etc.) not itself being critical. It is preferably an alcohol selected from the group comprising:

(a) alkanols having 1 to 4 C atoms and their oxethylates having preferably 1 to 20 ethylene oxide units per molecule;

(b) alkylene glycols having 2 to 4 C atoms in the alkylene group, their monoalkyl ethers having 1 to 4 C atoms in the alkyl group, and their oxethylates having preferably 1 to 20 ethylene oxide units per molecule;

(c) glycerol and its oxethylates having preferably 1 to 20 ethylene oxide units per molecule;

(d) polyglycerols, preferably diglycerol to decaglycerol, and their oxethylates having preferably 1 to 20 ethylene oxide units per molecule;

(e) erythritol and pentaerythritol and their oxethylates having preferably 1 to 20 ethylene oxide units per molecule;

(f) pentitols and hexitols, preferably mannitol, dulcitol, sorbitol, isosorbitol and sorbitan, and their oxethylates having preferably 1 to 20 ethylene oxide units per molecule; and (g) mono and disaccharides, preferably fructose, glucose, lactose, sucrose and their oxethylates having preferably 1 to 20 ethylene oxide units per molecule.

Particularly preferred alcohol components are glycerol, diglycerol to decaglycerol, sorbitol and sorbitan, and their oxethylates having 1 to 20 ethylene oxide units per molecule and the oxethylates of glucose, lactose and sucrose having 1 to 20 ethylene oxide units per molecule.

The process by which the esters have been prepared is not critical for the treatment according to the invention. They can be obtained by esterification and transesterification processes or also by reaction of acid anhydrides and alcohols, acid halides and alcohols, or nitriles and alcohols (cf. Ullmanns Enzyklopädie der technischen Chemie (Encyclopedia of Industrial Chemistry), volume 11, 4th edition, Verlag Chemie, Weinheim, Federal Republic of Germany; German Offenlegungsschrift No. 2,423,278 and U.S. Pat. No. 3,637,774). The esters to be treated according to the invention have preferably been prepared by the known and customary esterification and transesterification processes. In the preparation of the esters, mixtures of the particular starting substances, for example a mixture of carboxylic acids and of alcohols, can also be employed. It is of no consequence for the treatment according to the invention whether esters or mixed esters are present, or whether the esters or mixed esters have no free hydroxyl groups, or still have one or more free hydroxyl groups. They can also be modified esters, for example by oxethylation.

The process according to the invention has several advantages. It is simple and cheap, produces the desired purification effect and is, in addition, largely independent of the type, the constitution and the physical and chemical properties of the ester. It is used particularly advantageously to purify those esters which have already been prepurified by distillation, extraction and/or other separation processes, so that they still contain only relatively small amounts of alcohol, or to purify those esters which originate from a reaction of alcohol and acid carried out with stoichiometric amounts and thus contain little alcohol from the start.

The invention is now explained in more detail, using examples:

EXAMPLE 1

A crude ester was initially prepared by the known and customary reaction of 1 mole of diglycerol with 2 moles of isostearic acid. The crude ester obtained, which was liquid at room temperature, was very cloudy. 500 g of this crude ester were initially introduced into a 1 liter beaker provided with a stirrer and, at room temperature and with stirring, 0.5 g of methylhydroxyethylcellulose in the form of a powder (which is 0.1% by weight relative to the ester) was added. Subsequently, the mixture was stirred for a further 15 min. at room temperature, and then filtered. The originally cloudy ester was now a clear liquid.

EXAMPLE 2

A diglyceryl stearate-oxethylate was initially prepared by the known and customary procedure by reaction of 1 mole of diglycerol with 2 moles of stearic acid and subsequent oxethylation with 3 moles of ethylene oxide. The crude ester obtained, which was wax-like at room temperature, had a melting point of 50° to 60° C. and was a very cloudy liquid in the molten state. 1 kg of this crude ester was heated to 75° C. in a 2-liter beaker, 5 g of granulated carboxymethylhydroxypropylguar (which is 0.5% by weight relative to ester-oxethylate) were added, with stirring and maintaining 75° C., and stirring was continued at 75° C. for 30 min. The solid was then filtered off. The originally very cloudy ester was now a perfectly clear liquid in the molten state.

EXAMPLE 3

A crude glyceryl monostearate, which had been obtained by glycerinolysis of glyceryl tristearate by customary methods, after separating off the major part of the excess glycerol still contained 9% by weight of residual glycerol, and this was largely present in the monostearate in the dissolved form. 500 g of crude product was heated to 75° C. in a 2-1 beaker, and thus converted to a low-viscosity state. 50 g of carboxymethylcellulose in the form of a powder (which is 10% by weight relative to the crude ester) were then added, in portions, with stirring at 75° C., after which stirring was continued for 45 min. at 80° C. Subsequently, filtration was carried out at a temperature of 75° to 80° C. in order to maintain the low viscosity and thus the filterability. The orginally cloudy ester was now a completely clear product in the molten (liquid) state, and still contained only 2.7% by weight of dissvoled residual glycerol. This example was repeated using carboxymethylcellulose as a paste, which had been obtained by mixing 15 g of carboxymethylcellulose, in the form of a powder, with 25 ml of water. The residual content glycerol was only 3.2% by weight.

EXAMPLE 4

A crude ester was initially prepared by the known and customary reaction of 1 mole of pentaerythritol with 2 moles of oleic acid. It still contained about 5% by weight of solid unreacted pentaerythritol and was a relatively highly viscous and cloudy liquid at room temperature. Because of the very viscous state, the removal of the pentaerythritol by filtration at room temperature is not possible. On warming to about 80° C., the product does becomes more fluid and thus filterable, but this causes the pentaerythritol which is undissolved at room temperature, to dissolve, for which reason it also cannot be removed by filtration at elevated temperatures. However, with the process according to the invention it is possible to purify the crude ester from the pentaerythritol constituents, rapidly and in a simple manner, and to obtain a clear ester. 35 g of carboxymethyl starch in the form of a powder (which is 7% by weight relative to the crude ester) were added to 500 g of the crude ester in a 1-liter beaker, at 80° C. with stirring, and stirring was continued for 45 min. Subsequently, the solid was filtered-off hot (that is to say at 80° C.). The ester thus obtained was now a highly viscous clear liquid at room temperature.

EXAMPLE 5

A crude ester was initially prepared, in a known and customary procedure, by oxethylating sorbitol with 15 moles of ethylene oxide and then esterifying with 3 moles of lauric acid. The crude ester was highly viscous and very cloudy at room temperature. 500 g of the crude ester were initially introduced into a 1-liter flask equipped with a device for passing in nitrogen and a stirrer, and heated to 80° C. Then 10 g of hydroxyethyl starch in the form of a powder (which is 2% by weight relative to crude ester) were added slowly and the mixture was then stirred for a further 90 min. at 80° C. Then the solid was filtered off at 80° C. The liquid obtained was highly viscous and perfectly clear at room temperature.

EXAMPLE 6

Sucrose was oxethylated by customary methods with 9 moles of ethylene oxide and then esterified with 1 mole of isononanoic acid by known procedures to give a crude ester which was purified as follows:

200 g of the crude ester were initially introduced into a 500-ml flask (equipped with a device for passing in nitrogen and a stirrer). The crude ester was heated to 75° C., and 2 g of granulated carboxymethylhydroxypropylguar (which is 1% by weight relative to crude ester) were added, with stirring, and stirring was continued for 30 min at 75° C. The mixture was then filtered hot (at 75° C.). The product, which was viscous at room temperature, was clear.

We claim:

1. A process for the purification of a liquid ester of essentially an aliphatic carboxylic acid and a monohydric or polyhydric alcohol from the residual amounts of said alcohol which may be either dispersed or dissolved in the liquid ester, said process comprising:
   (a) adding to the liquid ester, while stirring, 0.01 to 20% by weight, relative to the weight of the ester to be purified, of a water-soluble etherified polysaccharide in a solid form and keeping the liquid ester in contact with the etherified polysaccharide for about 5 to about 120 minutes at about 15° to about 90° C. to take up said residual amounts of alcohol, and
   (b) separating the purified and still liquid ester from etherified polysaccharide in solid form,
said water-soluble etherified polysaccharide being selected from the group consisting of the alkyl, hydroxyalkyl, and carboxylalkyl ethers of cellulose, starch, and guar, wherein the alkyl group has 1 to 3, the hydroxyalkyl group has 2 to 4, and the carboxyalkyl group has 2 to 3 carbon atoms.

2. A process as claimed in claim 1 wherein the water-soluble etherified polysaccharide to be added is in the form of a powder or granules.

3. A process as claimed in claim 1, wherein the water-soluble etherified polysaccharide is added in an amount of 0.1 to 10 percent by weight, relative to the weight of the ester to be purified.

4. A process as claimed in claim 1, wherein the liquid ester to be purified is the reaction product of essentially a monocarboxylic fatty acid having 4 to 22 carbon atoms and an alcohol selected from the group consisting of
   (1) alkanols having 1 to 4 carbon atoms and their oxethylates having 1 to 29 ethylene oxide units per molecule;
   (2) alkylene glycols having 2 to 4 carbon atoms in the alkylene group, their monoalkyl ethers having 1 to 4 carbon atoms in the alkyl group, and their oxethylates having 1 to 20 ethylene oxide units per molecule;
   (3) glycerol and its oxethylates having 1 to 20 ethylene oxide units per molecule;
   (4) polyglycerols selected from the group consisting of diglycerol to decaglycerol and their oxethylates having 1 to 20 ethylene oxide units per molecule;
   (5) erythritol and pentaerythritol and their oxethylates having 1 to 20 ethylene oxide units per molecule;
   (6) hexitols selected from the group consisting of mannitol, dulcitol, sorbitol, isosorbitol, and sorbitan, and their oxethylates having 1 to 20 ethylene oxide units per molecule; and
   (7) mono- and disaccharides selected from the group consisting of fructose, glucose, lactose, sucrose, and their oxethylates having 1 to 20 ethylene oxide units per molecule.

5. A process as claimed in claim 1, wherein the ester to be purified is the reaction production of essentially a monocarboxylic fatty acid having 4 to 22 carbon atoms and of an alcohol selected from the group consisting of glycerol, diglycerol to decaglycerol, sorbitol and sorbitan as well as their oxethylates having 1 to 20 ethylene oxide units per molecule, and the oxethylates of glucose, lactose and sucrose having 1 to 20 ethylene oxide units per molecule.

6. Process as claimed in claim 1, wherein the still liquid ester is separated from the etherified polysaccharide by filtration.

7. A process as claimed in claim 1, wherein the still liquid ester is separated from the etherified polysaccharide by decantation.

8. A process as claimed in claim 1, wherein the liquid ester is essentially the reaction product of a monocarboxylic acid and a polyhydric alcohol.

* * * * *